(12) United States Patent
Stott (10) Patent No.: US 8,067,427 B2
(45) Date of Patent: Nov. 29, 2011

(54) PHARMACEUTICAL COMPOSITIONS COMPRISING ZD6474

(75) Inventor: Paul William Stott, Wilmington, DE (US)

(73) Assignee: AstraZeneca AB, Sodertajle (SE)

( * ) Notice: Subject to any disclaimer, the term of this patent is extended or adjusted under 35 U.S.C. 154(b) by 1178 days.

(21) Appl. No.: 11/596,979

(22) PCT Filed: May 18, 2005

(86) PCT No.: PCT/GB2005/001931
§ 371 (c)(1),
(2), (4) Date: Nov. 20, 2006

(87) PCT Pub. No.: WO2005/112934
PCT Pub. Date: Dec. 1, 2005

(65) Prior Publication Data
US 2007/0244323 A1  Oct. 18, 2007

(30) Foreign Application Priority Data
May 21, 2004  (GB) .................................. 0411378.3

(51) Int. Cl.
*A01N 43/54* (2006.01)
*A61K 31/517* (2006.01)
*C07D 239/70* (2006.01)

(52) U.S. Cl. ...................................... 514/266.1; 544/282
(58) Field of Classification Search .................. 544/282; 514/266.1
See application file for complete search history.

(56) References Cited

FOREIGN PATENT DOCUMENTS
EP          1 481 678       12/2004
WO      WO 98/13354    *    4/1998
WO      WO 01/32651         5/2001

OTHER PUBLICATIONS

Bates, David: "ZD-6474 AstraZeneca." Current Opinion in Investigational Drugs, 4(12): 1468-1472 (2003).
Lerk CF et al., "Effect of microcrystalline cellulose on liquid penetration in and disintegration of directly compressed tablets", J. Pharm. Sci., Feb. 1979, 68(2), 205-11.

* cited by examiner

*Primary Examiner* — Paul V. Ward
(74) *Attorney, Agent, or Firm* — Morgan, Lewis & Bockius LLP (57) ABSTRACT

A pharmaceutical composition comprising ZD6474 or a pharmaceutically acceptable salt thereof, a brittle diluent and a second diluent which is practically insoluble and has ductile compression properties.

6 Claims, 2 Drawing Sheets

PHARMACEUTICAL COMPOSITIONS COMPRISING ZD6474

CROSS-REFERENCE TO RELATED APPLICATIONS

This application is a national stage of PCT/GB2005/01931, filed May 18, 2005, which claims priority to United Kingdom Application Nos. 0411378.3 filed May 21, 2004.

BACKGROUND OF THE INVENTION

The present invention relates to pharmaceutical compositions, particularly to pharmaceutical compositions containing ZD6474 or a pharmaceutically-acceptable salt thereof, to processes for the preparation of said pharmaceutical compositions, to said pharmaceutical compositions for use in the production of an antiangiogenic and/or vascular permeability reducing effect in a warm-blooded animal such as a human, to the use of said pharmaceutical compositions in the manufacture of a medicament for use in the production of an antiangiogenic and/or vascular permeability reducing effect in a warm-blooded animal such as a human and to a method for the production of an antiangiogenic and/or vascular permeability reducing effect in a warm-blooded animal such as a human which comprises the administration of such a pharmaceutical composition.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacol. Sci. 16: 57-66; Folkman, 1995, Nature Medicine 1: 27-31). Alteration of vascular permeability is thought to play a role in both normal and pathological physiological processes (Cullinan-Bove et al, 1993, Endocrinology 133: 829-837; Senger et al, 1993, Cancer and Metastasis Reviews, 12: 303-324). Several polypeptides with in vitro endothelial cell growth promoting activity have been identified including, acidic and basic fibroblast growth factors (aFGF & bFGF) and vascular endothelial growth factor (VEGF). By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848-859; Kolch et al, 1995, Breast Cancer Research and Treatment, 36:139-155) and vascular permeability (Connolly et al, 1989, J. Biol. Chem. 264: 20017-20024). Antagonism of VEGF action by sequestration of VEGF with antibody can result in inhibition of tumour growth (Kim et al, 1993, Nature 362: 841-844).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity which leads to phosphorylation of tyrosine residues on both the receptor and other intracellular molecules. These changes in tyrosine phosphorylation initiate a signalling cascade leading to a variety of cellular responses. To date, at least nineteen distinct RTK subfamilies, defined by amino acid sequence homology, have been identified. One of these subfamilies is presently comprised by the fms-like tyrosine kinase receptor, Flt-1 (also referred to as VEGFR-1), the kinase insert domain-containing receptor, KDR (also referred to as VEGFR-2 or Flk-1), and another fms-like tyrosine kinase receptor, Flt-4. Two of these related RTKs, Flt-1 and KDR, have been shown to bind VEGF with high affinity (De Vries et al, 1992, Science 255: 989-991; Terman et al, 1992, Biochem. Biophys. Res. Comm. 1992, 187: 1579-1586). Binding of VEGF to these receptors expressed in heterologous cells has been associated with changes in the tyrosine phosphorylation status of cellular proteins and calcium fluxes.

VEGF is a key stimulus for vasculogenesis and angiogenesis. This cytokine induces a vascular sprouting phenotype by inducing endothelial cell proliferation, protease expression and migration, and subsequent organisation of cells to form a capillary tube (Keck, P. J., Hauser, S. D., Krivi, G., Sanzo, K., Warren, T., Feder, J., and Connolly, D. T., Science (Washington D.C.), 246: 1309-1312, 1989; Lamoreaux, W. J., Fitzgerald, M. E., Reiner, A., Hasty, K. A., and Charles, S. T., Microvasc. Res., 55: 29-42, 1998; Pepper, M. S., Montesano, R., Mandroita, S. J., Orci, L. and Vassalli, J. D., Enzyme Protein, 49: 138-162, 1996.). In addition, VEGF induces significant vascular permeability (Dvorak, H. F., Detmar, M., Claffey, K. P., Nagy, J. A., van de Water, L., and Senger, D. R., (Int. Arch. Allergy Immunol., 107: 233-235, 1995; Bates, D. O., Heald, R. I., Curry, F. E. and Williams, B. J. Physiol. (Lond.), 533: 263-272, 2001), promoting formation of a hyper-permeable, immature vascular network which is characteristic of pathological angiogenesis.

It has been shown that activation of KDR alone is sufficient to promote all of the major phenotypic responses to VEGF, including endothelial cell proliferation, migration, and survival, and the induction of vascular permeability (Meyer, M., Clauss, M., Lepple-Wienhues, A., Waltenberger, J., Augustin, H. G., Ziche, M., Lanz, C., Büttner, M., Rziha, H-J., and Dehio, C., EMBO J., 18: 363-374, 1999; Zeng, H., Sanyal, S. and Mukhopadhyay, D., J. Biol. Chem., 276: 32714-32719, 2001; Gille, H., Kowalski, J., Li, B., LeCouter, J., Moffat, B, Zioncheck, T. F., Pelletier, N. and Ferrara, N., J. Biol. Chem., 276: 3222-3230, 2001).

Quinazoline derivatives which are inhibitors of VEGF receptor tyrosine kinase are described in International Patent Applications Publication Nos. WO 98/13354 and WO 01/32651. In WO 98/13354 and WO 01/32651 compounds are described which possess activity against VEGF receptor tyrosine kinase (VEGF RTK) whilst possessing some activity against epidermal growth factor (EGF) receptor tyrosine kinase (EGF RTK).

ZD6474 is 4-(4-bromo-2-fluoroanilino)-6-methoxy-7-(1-methylpiperidin-4-ylmethoxy)quinazoline:

ZD6474

ZD6474 falls within the broad general disclosure of WO 98/13354 and is exemplified in WO 01/32651 (Example 2 therein). ZD6474 is a potent inhibitor of VEGF RTK and also has some activity against EGF RTK. ZD6474 has been shown to elicit broad-spectrum anti-tumour activity in a range of models following once-daily oral administration (Wedge S. R., Ogilvie D. J., Dukes M. et al, Proc. Am. Assoc. Canc. Res. 2001; 42: abstract 3126).

In WO 98/13354, Example 77 therein describes some pharmaceutical dosage forms of a compound of formula I. In WO 01/32651, Example 11 therein describes similar pharmaceutical dosage forms of a compound of formula I. WO 01/32651 also describes the formulation of compounds that was used for dosing rats in the 14 day toxicity test: "Compounds were initially formulated by suspension in a 1% (v/v) solution of polyoxyethylene (20) sorbitan mono-oleate in deionised water, by ball-milling at 4° C. overnight (at least 15 hours). Compounds were re-suspended by agitation immediately prior to dosing."

In general, pharmaceutical compositions of the compounds of formula I in WO 01/32651 may be prepared in a conventional manner using conventional excipients. An oral dosage form (e.g. tablet, capsule, granules, pellets, lozenges etc.) of ZD6474 was sought for clinical trials and commercial use.

In developing an oral dosage form, particularly tablets, one must consider the mechanical properties of the active pharmaceutical ingredient and of any proposed excipients.

The mechanical properties of materials such as powders may be described in terms of the following characteristics:
(a) Hardness, or resistance to deformation, which can be measured by an indentation hardness test;
(b) Yield pressure (denoted Py and also known as yield stress), that is the point at which plastic deformation occurs, which can be measured by compaction studies;
(c) Strain Rate Sensitivity (SRS), that is the percent increase in yield pressure from slow to fast punch velocity, which can be measured by compaction studies; and
(d) Modulus of Elasticity, that is the ratio of stress to elongation (strain), which can be measured by numerous methods that are well known to a person skilled in the art of formulation.

Materials can, in general, be classified by the way in which they deform under compressive force, either by brittle fracture or by plastic deformation. The degree of deformation for a brittle material is independent of the rate and duration of the compression event (that is the compression applied), giving a strain rate sensitivity value for such materials of 0% (zero %). Deformation of a plastic material is dependent on the rate and duration of the compression event and this is described by the strain rate sensitivity.

When developing an oral dosage form, particularly a tablet formulation, it is usual to use a mixture of powders: some with brittle character to minimise the strain rate sensitivity and some with moderate plastic character to increase the surfaces available to form bonds during compression.

Tablet presses used in commercial manufacture typically run at much faster speeds than those used in research and development. As the speed of a press increases, the duration of the compression event (that is the period for which compression is applied; also known as dwell time) decreases. This has no impact on the compression of a brittle material with an SRS of say 0%, but for a plastic material, for which the deformation is dependent on the rate and duration of compression, a faster press would typically produce softer tablets. Therefore, an excess of plastic material in a formulation can lead to difficulties on scale up to the faster compression machines used in full scale production.

ZD6474 is an extremely plastic material with a yield pressure of 22 MPa and with a very high strain rate sensitivity of 197%. This makes the formulation of a solid oral dosage form of ZD6474 difficult. For example in tablet manufacture these properties can lead to problems in achieving suitably hard tablets, particularly when scaling up from the relatively slow tablet machines (with correspondingly long compression events) used in research and development for small numbers of tablets, to the faster compression machines (with short compression events) used in full scale commercial manufacture.

BRIEF SUMMARY OF THE INVENTION

The object of the present invention is to provide pharmaceutical compositions of ZD6474 that have the required good compression properties, requisite hardness, resistance to friability, and that have the required good disintegration and dissolution properties, that allow high drug loading, and that do no cap when made into tablets.

According to the present invention there is provided a pharmaceutical composition comprising ZD6474 or a pharmaceutically acceptable salt thereof, a brittle diluent and a second diluent which is practically insoluble and has ductile compression properties.

DETAILED DESCRIPTION OF THE INVENTION

In order to counteract the plasticity of a drug such as ZD6474 a person skilled in the art would typically try to 'dilute' the material with large quantities of a complementary excipient such as a brittle excipient. However this can limit the drug loading that can be achieved in a formulation, i.e. the percentage of active ingredient therein, and can lead to very large tablets which are difficult to swallow.

A standard brittle filler, heavy magnesium carbonate, was used in the initial test formulation of ZD6474 to counteract the plasticity and high strain rate sensitivity of ZD6474. The test formulation comprised:

Composition of ZD6474 100 mg tablet cores
(magnesium carbonate formulation)

| Ingredient | mg/tablet | Function |
|---|---|---|
| ZD6474 | 100.0 | Active agent |
| Heavy magnesium carbonate | 262.8 | Diluent |
| Hydroxypropylmethylcellulose (HPMC 606) | 16.0 | Binder |
| Croscarmellose sodium (Ac-di-sol) | 16.0 | Disintegrant |

| Composition of ZD6474 100 mg tablet cores (magnesium carbonate formulation) | | |
|---|---|---|
| Ingredient | mg/tablet | Function |
| Sodium lauryl sulphate (SLS) | 1.2 | Wetting agent |
| Magnesium stearate | 4.0 | Lubricant |
| Total compression weight | 400.0 mg | |

Unfortunately the magnesium carbonate formulation did not have the required disintegration and dissolution properties for formulating tablets, because on storage of this formulation under conditions of high humidity (75% relative humidity) and high temperature (40° C.) it was found that the tablets had very prolonged disintegration times (greater than 30 minutes) and failed on dissolution testing.

ZD6474 is poorly soluble in water (0.033 mg/ml at 25° C.) and per the British Pharmacopoeia 2001-2002 classification system (see Table 1 hereinafter) it can be described as a 'practically insoluble' or 'insoluble' compound. Typically when formulating a practically insoluble drug, soluble diluents are included in order to increase the dissolution rate. In order to improve the dissolution of the ZD6474, a further formulation was prepared with the freely soluble diluent lactose monohydrate. Lactose monohydrate was chosen because it is a freely soluble filler but also because it has a relatively low strain rate sensitivity of 19.4% and is therefore also a relatively brittle filler. This test formulation comprised:

| Composition of ZD6474 200 mg tablet cores (lactose monohydrate formulation) | | |
|---|---|---|
| Ingredient | mg/tab | Function |
| ZD6474 | 200.0 | Active agent |
| Lactose monohydrate (450 mesh) | 356.2 | Diluent |
| Croscarmellose sodium (Ac-di-sol) | 24.0 | Disintegrant |
| Povidone | 12.0 | Binder |
| Sodium lauryl sulphate | 1.8 | Wetting agent |
| Magnesium stearate | 6.0 | Lubricant |
| Total | 600.0 | |

On manufacture and stability testing of the lactose monohydrate formulation it was noted that whilst adequate disintegration and dissolution could be achieved the tablets were soft, had a poor appearance and were damaged by subsequent processing and handling. These problems were found using relatively slow compression machines in development; they would be exacerbated on scale up to faster compression machines. Further, the maximum drug loading that could be achieved with this formulation and still produce a tablet which did not 'cap' was 33%. Drug loading is required to be as high as possible in order to minimise the size of the individual tablet.

In order to try to resolve the problems of plasticity and dissolution in a single formulation a further formulation was produced comprising a brittle filler to improve compression properties and a freely soluble filler to improve disintegration and dissolution properties.

For this formulation the brittle filler used was dibasic calcium phosphate and the freely soluble filler was lactose monohydrate. This test formulation comprised:
Composition of ZD6474 400 mg Tablet Cores (Calcium Phosphate/lactose Monohydrate Formulation)

| Ingredient | mg/tab | Function |
|---|---|---|
| ZD6474 | 400.0 | Active agent |
| Dibasic calcium phosphate | 317 | Diluent |
| Lactose monohydrate | 200 | Diluent |
| Sodium starch glycollate | 50 | Disintegrant |
| Povidone | 20 | Binder |
| Sodium lauryl sulphate | 3 | Wetting agent |
| Magnesium stearate | 10 | Lubricant |
| Total | 1000.0 mg | |

Figure 1:
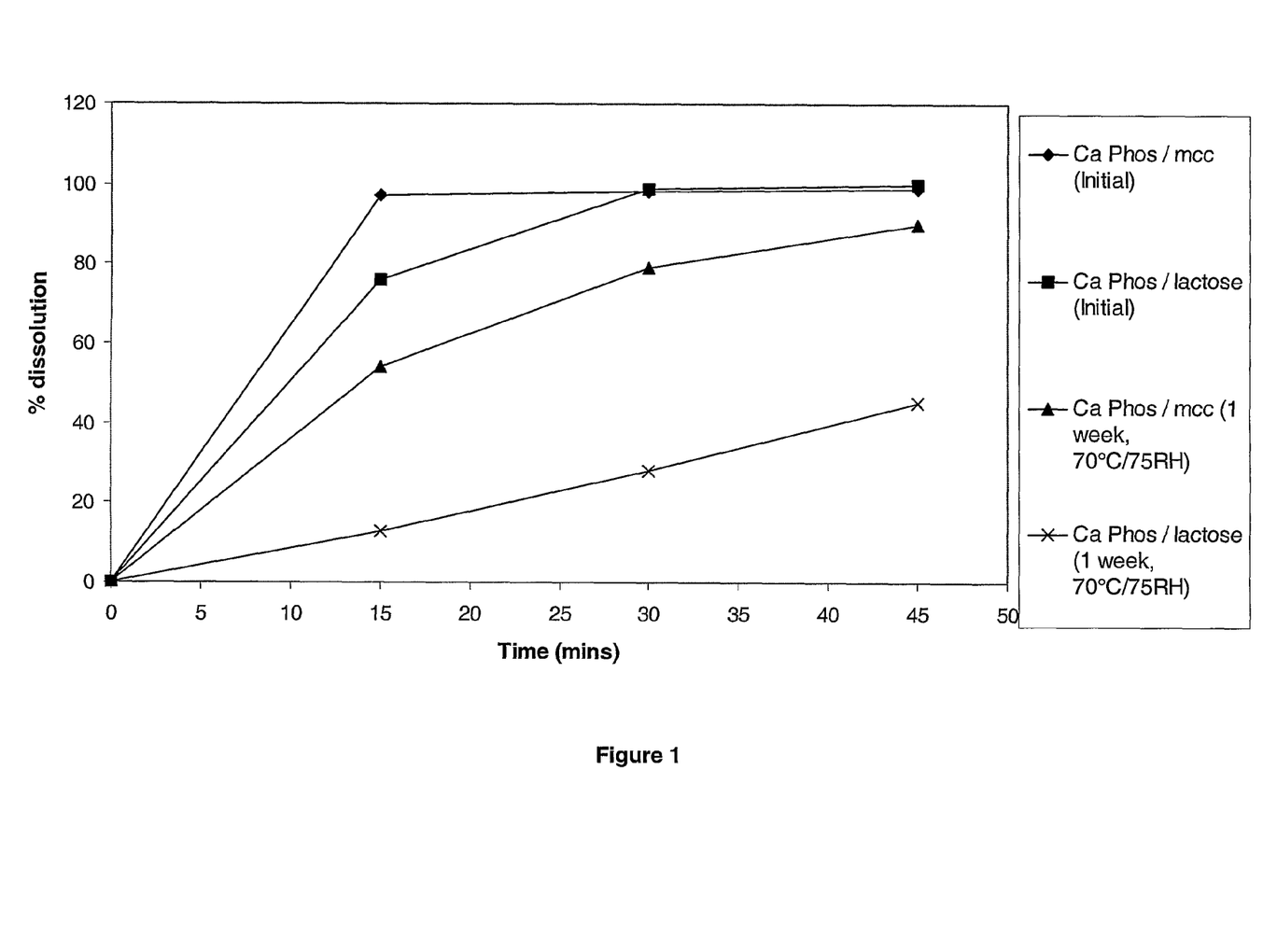
FIG. 1 shows a comparison of the dissolution profiles of ZD6474 100 mg tablets of an example of the present invention (containing dibasic calcium phosphate and microcrystalline cellulose (mcc)) and a calcium phosphate/lactose monohydrate formulation, before and after storage at 70° C./75% relative humidity (RH) for 7 days.

However, on storage at high humidity (75% relative humidity) and high temperature (70° C.) this formulation also gave prolonged disintegration and dissolution times (see FIG. 1).

The object of the present invention is to provide pharmaceutical compositions of ZD6474 that have the required good compression properties, requisite hardness, resistance to friability, and that have the required good disintegration and dissolution properties, that allow high drug loading, and that do not cap when made into tablets.

Preferably the pharmaceutical compositions of ZD6474 are solid oral dosage forms of ZD6474, particularly tablets of ZD6474.

Surprisingly, we have now found that a formulation of ZD6474 with a brittle filler as the principal excipient and a second filler which is practically insoluble and has ductile compression properties, has particularly advantageous properties. One would expect that a 15 practically insoluble filler would give prolonged disintegration and dissolution times compared to a freely soluble filler (e.g. lactose monohydrate) and one would expect that adding further ductile material to a formulation of ZD6474 would be detrimental to the compression properties. However, unexpectedly and surprisingly, we have found that addition of a ductile second filler with a relatively high SRS to a ZD6474 formulation including a brittle filler gives improved compression properties in terms of hardness and resistance to capping.

FIG. 1 shows a comparison of the dissolution profiles of ZD6474 tablets of an example of the present invention (containing dibasic calcium phosphate and microcrystalline cellulose (mcc)) and the calcium phosphate/lactose monohydrate formulation described above, before and after storage at 70° C./75% relative humidity (RH) for 7 days (examples shown are for 100 mg variants).

The data indicate that the formulation containing the practically insoluble microcrystalline cellulose produces a more rapid dissolution and is more stable after storage at high temperature and humidity.

According to the present invention there is provided a pharmaceutical composition comprising ZD6474 or a pharmaceutically acceptable salt thereof, a brittle diluent and a second diluent which is practically insoluble and has ductile compression properties.

A brittle diluent or filler is preferably an inorganic calcium- or magnesium-containing compound such as dibasic calcium phosphate, tribasic calcium phosphate, calcium phosphate anhydrous, calcium carbonate, calcium sulphate or magnesium oxide.

In one aspect of the present invention the brittle diluent is dibasic calcium phosphate.

In another aspect of the present invention the brittle diluent is tribasic calcium phosphate.

Practically insoluble diluents or fillers with ductile compression properties include microcrystalline cellulose (mcc), starch, ethylcellulose and carboxymethylcellulose.

In one aspect of the present invention the practically insoluble diluent with ductile compression properties is microcrystalline cellulose.

Suitably, the weight ratio of ZD6474 or a pharmaceutically acceptable salt thereof to the brittle filler is from 1:0.5 to 1:7, for example from 1:1 to 1:6, more particularly from 1:1 to 1:4, still more particularly from 1:1 to 1:2.

Suitably, the weight ratio of the practically insoluble filler with ductile compression properties to the brittle filler is from 1:3 to 1:12, for example from 1:3.5 to 1:10, more particularly from 1:4 to 1:4.5.

Suitably the pharmaceutical composition contains for example, from 20 to 80%, particularly from 30 to 55%, more particularly from 40 to 50%, especially from 40 to 45% by weight, based upon the total weight of the composition, of a brittle diluent.

Suitably the pharmaceutical composition contains for example, from 0.1 to 30%, preferably from 2 to 15%, particularly from 3 to 12%, more particularly from 4 to 11%, especially from 5 to 10% by weight, based upon the total weight of the composition, of a practically insoluble diluent with ductile compression properties.

The pharmaceutical compositions of the present invention are advantageously presented in unit dosage form. ZD6474 will normally be administered to a warm-blooded animal at a unit dose within the range 5-5000 mg per square metre body area of the animal, i.e. approximately 0.1-100 mg/kg. A unit dose in the range, for example, 1-100 mg/kg, preferably 1-50 mg/kg is envisaged and this normally provides a therapeutically-effective dose. A unit dose form such as a tablet or capsule will usually contain, for example 1-500 mg of active ingredient, preferably 40-400 mg.

Thus the composition may contain from 1 mg to 500 mg of ZD6474 or a pharmaceutically acceptable salt thereof. Suitable quantities of ZD6474 or a pharmaceutically acceptable salt thereof include, for example, 1, 10, 50, 100, 150, 200, 250, 300, 350, 400, 450 or 500 mg, depending upon the dose required and the particular form of the pharmaceutical composition. In one aspect of the present invention the pharmaceutical composition contains 50, 100, 150, 200, 300 or 400 mg of ZD6474 or a pharmaceutically acceptable salt thereof.

Typically ZD6474 or a pharmaceutically acceptable salt thereof will be present in an amount within the range of from 1 to 99%, and suitably from 1 to 70%, for example from 5 to 65% and especially from 10 to 60% by weight of the pharmaceutical composition.

According to another aspect of the present invention there is provided a pharmaceutical composition comprising ZD6474 or a pharmaceutically acceptable salt thereof, a brittle diluent, a second diluent which is practically insoluble and has ductile compression properties and a disintegrant.

Suitable disintegrants include those known in the art of formulation, such as those listed in The Handbook of Pharmaceutical Excipients, 4$^{th}$ edition, eds Rowe, R. C. et al, Pharmaceutical Press, 2003. Preferred disintegrants include sodium starch glycollate, crospovidone, croscarmellose sodium and starch.

A suitable weight ratio of ZD6474 or a pharmaceutically acceptable salt thereof to disintegrant is from 2:1 to 20:1, particularly from 3:1 to 15:1, more particularly from 4:1 to 10:1 and still more particularly from 6:1 to 9:1.

Suitably the pharmaceutical composition will contain from 0.01 to 10%, for example from 1 to 8%, particularly from 2 to 7% and more particularly from 3 to 6% by weight of disintegrant.

Other additional excipients may optionally be included in a pharmaceutical composition according to the present invention. Additional excipients include for example, binders, wetting agents and lubricants.

According to another aspect of the present invention there is provided a pharmaceutical composition comprising ZD6474 or a pharmaceutically acceptable salt thereof, a brittle diluent, a second diluent which is practically insoluble and has ductile compression properties, a disintegrant and one or more of a wetting agent, a binder and a lubricant.

According to another aspect of the present invention there is provided a solid pharmaceutical composition for oral administration comprising ZD6474 or a pharmaceutically acceptable salt thereof, a brittle diluent, a second diluent which is practically insoluble and has ductile compression properties, a disintegrant and one or more of a wetting agent, a binder and a lubricant.

Suitably one or more binders will be present in an amount of from 0.5 to 50% by weight, for example from 1 to 10% by weight.

Suitably one or more wetting agents will be present in an amount of from 0.01 to 10%, for example from 0.01 to 1% by weight.

Suitably one or more lubricants will be present in an amount of from 0.1 to 10% by weight, for example from 0.5 to 1.5% by weight.

Further additional excipients which may be added include preservatives, stabilisers, anti-oxidants, silica flow conditioners, antiadherents or glidants.

A particular pharmaceutical composition of the present invention comprises:
(a) from 1 to 70 (particularly from 5 to 50) parts ZD6474 or a pharmaceutically acceptable salt thereof;
(b) from 1 to 96 (particularly from 10 to 70) parts of a brittle diluent; and
(c) from 0.1 to 20 (particularly from 1 to 15) parts of a second diluent which is practically insoluble and has ductile compression properties;
wherein all parts are by weight and the sum of the parts (a)+(b)+(c)=100.

Another particular pharmaceutical composition of the present invention comprises:
(a) from 1 to 70 (particularly from 5 to 50) parts ZD6474 or a pharmaceutically acceptable salt thereof;
(b) from 1 to 96 (particularly from 10 to 70) parts of a brittle diluent;
(c) from 0.1 to 20 (particularly from 1 to 15) parts of a second diluent which is practically insoluble and has ductile compression properties;
(d) from 0.1 to 12 (particularly from 1 to 10) parts of a disintegrant;
(e) from 0 to 5 (particularly from 0 to 2) parts of a wetting agent;
(f) from 0.01 to 8 (particularly from 0.05 to 5) parts of a binder; and
(g) from 0.01 to 8 (particularly from 0.05 to 5) parts of a lubricant;
wherein all parts are by weight and the sum of the parts (a)+(b)+(c)+(d)+(e)+(f)+(g)=100.

When the pharmaceutical composition according to the invention is a solid dosage form such as a tablet, pellet or granules the solid composition optionally further comprises a suitable coating, for example a film coating. A coating can be used to provide protection against, for example, moisture ingress or degradation by light, to colour the formulation, or to modify or control the release of ZD6474 from the formulation.

According to one aspect of the present invention there is provided a pharmaceutical composition comprising a core comprising ZD6474 or a pharmaceutically acceptable salt thereof, a brittle diluent and a second diluent which is practically insoluble and has ductile compression properties and a coating.

The term 'good compression properties' relates to the mechanical properties of a material or mixture of powdered components. A material with good compression properties will consolidate under compressive force to form a "compact" which is of the requisite hardness, is not prone to damage during mechanical agitation, is not prone to capping, and can be formed at higher processing speeds where strain rates are higher and time available for compression is shorter.

The term 'requisite hardness' means sufficient mechanical strength, which will prevent a compact from becoming damaged during subsequent processing or transport. This is related to the size of the tablet and when measured in kiloponds (kp) is typically at least 0.8×the diameter of the tablet (mm), preferably at least 1×tablet diameter, more preferably at least 1.1×tablet diameter, particularly at least 1.2× tablet diameter, especially at least 1.3×tablet diameter. The greater the hardness the more robust the tablet is but at very high levels of hardness disintegration times can be unduly long.

The term 'capping' means the complete or partial separation of a saucer-shaped disc from the top or bottom surface of a tablet during compression of the material to form a tablet or during subsequent processes and/or handling. Capping is described in Carstensen, J. T., Solid pharmaceutics: mechanical properties and rate phenomena., Academic press, New York (1980) and in Sheth et al., Pharmaceutical dosage forms: Tablets. Vol 1. Ed Liebermann and Lachmann, Pub. Marcel Dekker, New York (1980).

The term 'friability' means the phenomenon whereby tablet surfaces are damaged and/or show evidence of cracking or breakage when subjected to mechanical agitation (e.g. during processing, handling or transportation).

The term "disintegration" means the process whereby a tablet breaks down into its constituent particles when in contact with a fluid.

The term "appropriate disintegration time" means for example a disintegration time of less than 12 minutes, advantageously less than 10 minutes, conveniently less than 9 minutes, preferably less than 8 minutes, more preferably less than 7 minutes, particularly less than 6 minutes, more particularly less than 5 minutes and especially less than 4 minutes.

The term "dissolution" means the process by which drug particles dissolve. In order for a drug to be absorbed it must first be dissolved in the fluid at the site of absorption.

The term "high drug loading" means that tablets of a high dosage, e.g. greater than 300 mg, can be made of a size that patients can swallow. For example, a drug loading of 40% ZD6474 produces a 200 mg tablet with a compression weight, i.e. total weight of the tablet, of 500 mg which is 11 mm in diameter.

The term 'brittle' as in 'brittle diluent' means that the material has a yield pressure (Py) of greater than 300 MPa and/or a strain rate sensitivity of from 0 to 10%.

The term 'ductile' as in 'ductile compression properties' means that the material has a yield pressure of less than 150 MPa, preferably less than 120 MPa, especially less than 100 MPa and/or has a strain rate sensitiviy of from 10 to 150%, preferably from 10 to 100%, especially from 30 to 80%.

The terms 'freely soluble' and 'practically insoluble' are as described by the British Pharmacopoeia 2001-2002 and are used to describe the amount of solute (material) that can be dissolved in water at temperatures between 15 and 25° C. The complete set of definitions is shown in Table 1.

TABLE 1

| Aqueous solubility definitions | | |
|---|---|---|
| Descriptive term | Approximate volume of water in millilitres per gram of solute | Milligrams per millilitre (mg/ml) |
| Very soluble | Less than 1 | >1000 |
| Freely soluble | From 1 to 10 | 100 to 1000 |
| Soluble | From 10 to 30 | 33.3 to 100 |
| Sparingly soluble | From 30 to 100 | 10 to 33.3 |
| Slightly soluble | Form 100 to 1000 | 1 to 10 |
| Very slightly soluble | Form 1000 to 10000 | 0.1 to 1 |
| Practically insoluble or insoluble | More than 10000 | <0.1 |

The present invention relates to pharmaceutical compositions comprising ZD6474 or a pharmaceutically acceptable salt thereof.

Salts of ZD6474 for use in pharmaceutical compositions will be pharmaceutically acceptable salts, but other salts may be useful in the production of ZD6474 and its pharmaceutically acceptable salts. Such salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methyl amine, dimethylamine, trimethylamine, piperidine, morpholine or tris-(2-hydroxyethyl)amine.

ZD6474 may be synthesised according to any of the known processes for making ZD6474. For example ZD6474 may be made according to any of the processes described in WO 01/32651; for example those described in Examples 2(a), 2(b) and 2(c) of WO 01/32651.

Preferably ZD6474 anhydrous free base is used for preparing the pharmaceutical compositions of the present invention.

The pharmaceutical compositions of the present invention may be prepared by conventional wet granulation, or dry blending, compression and then optionally, if a coating is desired, with film coating processes.

According to the present invention there is provided a process for the manufacture of a pharmaceutical composition comprising ZD6474 or a pharmaceutically acceptable salt thereof, comprising:
  (a) mixing ZD6474, a brittle diluent, a second diluent which is practically insoluble and has ductile compression properties, and optionally other excipients, to produce a homogeneous mix;
  (b) adding a suitable liquid to the powders with mixing until a suitable wet mass is obtained;
  (c) drying the mixture.

According to the present invention there is provided a process for the manufacture of a pharmaceutical composition comprising ZD6474 or a pharmaceutically acceptable salt thereof, comprising:
  (a) mixing ZD6474, a brittle diluent such as dibasic calcium phosphate, a second diluent which is practically insoluble and has ductile compression properties, such as microcrystalline cellulose, optionally with other diluents such as crospovidone and povidone, together in a suitable vessel, such as a high shear granulator, to produce a homogeneous mix;
  (b) adding a suitable liquid to the powders with mixing until a suitable wet mass is obtained;

(c) passing the wet granules through a suitable screen to remove large particles;

(d) drying the mixture;

(e) passing the dried granules so formed through a further screen and blending the mixture with a suitable lubricant such as magnesium stearate.

The resultant powder may be compressed into tablet cores, which can then, if desired, be coated using a conventional pan coater. The film coat may be applied by spraying an aqueous suspension of the coating ingredients onto the tablet cores.

A further process for the manufacture of a pharmaceutical composition comprising ZD6474 or a pharmaceutically acceptable salt thereof is provided, comprising: mixing ZD6474, a brittle diluent, such as dibasic calcium phosphate, a second diluent which is practically insoluble and has ductile compression properties, such as microcrystalline cellulose, optionally with other diluents such as crospovidone and povidone, together in a suitable vessel to produce a homogeneous mix.

The dry powder so formed may be compressed into tablet cores.

Alternatively the powder may be formed into granules by a dry granulation technique, e.g. roller compaction, and the resultant granules compressed into tablet cores.

The formulated pharmaceutical compositions may be made into tablets or granules or capsules and may be tested using the methods detailed below.

Dissolution Test Method

The dissolution of ZD6474 tablets were tested using the method described in Table 2. A tentative evaluation criterion Q=75% at 45 minutes, wherein Q is the percentage of ZD6474 released at a given time, was applied.

TABLE 2

| Apparatus | USP equipment - Teflon coated paddles, clear glass dissolution pots, six position minimum. United States Pharmacopoeia Method II (paddle) |
|---|---|
| Medium volume | 1000 ml |
| Dissolution medium | 0.5% sodium lauryl sulphate (SLS) solution |
| Stirring speed | 100 rpm |
| Temperature | 37.0° C. ± 0.5° C. |
| Sampling volume | 10 ml |
| Sampling times | 15, 30, 45, 60 minutes* |

*additional time points of 5, 10 and 90 minutes have been used for tablets that had a process or formulation change.

Dissolution Medium Preparation

Two litres of 5% SLS medium was prepared, e.g. by dissolving 100 g of sodium lauryl sulphate (aka sodium dodecyl sulphate) in 2 litres of water, stirring continuously for about 30 minutes. Then preparing a suitable amount of 0.5% SLS medium by diluting the 5% SLS media by a factor of 10, e.g. 2 litres of 5% SLS diluted to 20 litres with water, to give 20 litres of 0.5% SLS medium.

Disintegration Test Method

The disintegration time of 6 individual tablets was determined, as described in Test A, in the European Pharmacopoeia (Ph Eur 2002), using water as the immersion fluid and omitting the discs. The time (minutes) at which all 6 tablets disintegrated was recorded.

Disintegration is considered to be achieved when:
(i) no residue remains on the screen, or
(ii) if there is a residue, it consists of a soft mass having no palpably firm, unmoistened core, or
(iii) only fragments of coating remain.

The tablets pass the test if all six have disintegrated within 30 minutes. If any of the tablets have not disintegrated within 30 minutes, the test is repeated on a further six tablets using 0.1M HCl as disintegration medium.

Yield Pressure Test Method

The yield pressure of a material can be determined by compressing it in a compaction simulator using a simple uniaxial saw tooth displacement/time profile and measuring the corresponding forces. The compaction simulator is fitted with 10 mm flat-faced punches and the material is compressed to zero porosity at a specific punch velocity. The force/displacement data generated are manipulated to produce a Heckel plot and the yield pressure is equivalent to the reciprocal of the straight portion of the Heckel plot. This test can be performed at different punch velocities to determine the effect of scale-up on the deformation characteristics of the material.

Heckel Equation $$\ln\left(\frac{1}{1-D}\right) KP + A$$

where K and A are constants obtained from the slope and intercept of the plot D is the relative density at pressure P.

(Ref: Roberts, R. J. and Rowe, R. C., The effect of punch velocity on the compaction of a variety of materials. J. Pharm. Pharmacol., 37 (1985) 377-384)

Strain Rate Sensitivity (SRS)

The strain rate sensitivity of a material can be calculated using the mean yield pressures (Py) calculated for a material at fast (300 mm s$^{-1}$) and slow (0.033 mm s$^{-1}$) punch velocities.

$$SRS = \frac{Py_{300} - Py_{0.033}}{Py_{0.033}} \times 100$$

(Ref: Rowe, R. C., Roberts, R. J., Chapter 1, pg 34 in Advances in Pharmaceutical Sciences. Eds Ganderton, Jones, McGinity. Vol. 7 1995)

Hardness Test Procedure (300 mg Tablets)

The hardness of 15 individual tablets, selected from a batch at random, were measured using a Schleuniger Hardness Tester Model 6D or equivalent. The hardness of each tablet was measured along its diameter. The average 'hardness' is reported in kiloponds (kP).

Friability Test Method

Twenty tablets were accurately weighed and placed in a rotating drum (Copley TA-10 or equivalent). The drum was rotated 100 times and the tablets removed. Loose dust was removed from the tablets and the tablets re-weighed. The friability is expressed as the loss of mass and it is calculated as a percentage of the initial mass.

The pharmaceutical compositions of the present invention are preferably formulated into tablets but may be made into another form: suitable for oral administration, (for example pellets, granules, lozenges, hard or soft capsules, dispersible powders or granules); or for vaginal or rectal administration (for example as a pessary or a suppository).

As stated above the size of the dose of ZD6474 required for the therapeutic or prophylactic treatment of a particular disease state will necessarily be varied depending on the host treated, the route of administration and the severity of the illness being treated. Preferably a daily dose in the range of 1-50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a pharmaceutical composition comprising ZD6474 or a pharmaceutically acceptable salt thereof according to the present invention as described hereinbefore, for use in a method of treatment of the human or animal body by therapy.

Pharmaceutical compositions of the present invention inhibit VEGF receptor tyrosine kinase activity and are therefore of interest for their antiangiogenic effects and/or their ability to cause a reduction in vascular permeability.

A further feature of the present invention is a pharmaceutical composition comprising ZD6474 or a pharmaceutically acceptable salt thereof according to the present invention as described hereinbefore, for use as a medicament, conveniently a pharmaceutical composition comprising ZD6474 or a pharmaceutically acceptable salt thereof according to the present invention as described hereinbefore, for use as a medicament for producing an antiangiogenic and/or vascular permeability reducing effect in a warm-blooded animal such as a human being.

Thus according to a further aspect of the present invention there is provided the use of a pharmaceutical composition comprising ZD6474 or a pharmaceutically acceptable salt thereof according to the present invention as described hereinbefore in the manufacture of a medicament for use in the production of an antiangiogenic and/or vascular permeability reducing effect in a warm-blooded animal such as a human being.

According to a further feature of the present invention there is provided a method for producing an antiangiogenic and/or vascular permeability reducing effect in a warm-blooded animal, such as a human being, in need of such treatment which comprises administering to said animal an effective amount of a pharmaceutical composition comprising ZD6474 or a pharmaceutically acceptable salt thereof according to the present invention as described hereinbefore.

As stated above the pharmaceutical compositions of the present invention as defined herein are of interest for their antiangiogenic and/or vascular permeability effects. Angiogenesis and/or an increase in vascular permeability is present in a wide range of disease states including cancer (including leukaemia, multiple myeloma and lymphoma), diabetes, psoriasis, rheumatoid arthritis, Kaposi's sarcoma, haemangioma, acute and chronic nephropathies, atheroma, arterial restenosis, autoimmune diseases, acute inflammation, lymphoedema, endometriosis, dysfunctional uterine bleeding and ocular diseases with retinal vessel proliferation including age-related macular degeneration. Pharmaceutical compositions of the present invention are expected to be particularly useful in the prophylaxis and treatment of diseases such as cancer and Kaposi's sarcoma. In particular pharmaceutical compositions of the invention are expected to slow advantageously the growth of primary and recurrent solid tumours of, for example, the colon, pancreas, bladder, breast, prostate, lungs and skin. More especially pharmaceutical compositions of the present invention are expected to slow advantageously the growth of tumours in colorectal cancer and in lung cancer, for example mesothelioma and non-small cell lung cancer (NSCLC). More particularly pharmaceutical compositions of the invention are expected to inhibit any form of cancer associated with VEGF including leukaemia, multiple myeloma and lymphoma and also, for example, to inhibit the growth of those primary and recurrent solid tumours which are associated with VEGF, especially those tumours which are significantly dependent on VEGF for their growth and spread, including for example, certain tumours of the colon (including rectum), pancreas, bladder, breast, prostate, lung, vulva, skin and particularly NSCLC.

In another aspect of the present invention the pharmaceutical compositions of the present invention as defined herein are expected to inhibit the growth of those primary and recurrent solid tumours which are associated with VEGF especially those tumours which are significantly dependent on VEGF for their growth and spread.

In another aspect of the present invention the pharmaceutical compositions of the present invention as defined herein are expected to inhibit the growth of those primary and recurrent solid tumours which are associated with both VEGF and EGF especially those tumours which are significantly dependent on VEGF and EGF for their growth and spread.

The pharmaceutical compositions of the present invention as defined herein may be administered as a sole therapy or may involve, in addition to a composition of the present invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the antiangiogenic and/or vascular permeability reducing treatment defined hereinbefore may be: surgery, radiotherapy or chemotherapy.

Surgery may comprise the step of partial or complete tumour resection, prior to, during or after the administration of a pharmaceutical composition as described herein.

Other chemotherapeutic agents for optional use with a pharmaceutical composition of the present invention as defined herein include those described in WO 01/32651 which is incorporated herein by reference. Such chemotherapy may cover five main categories of therapeutic agent:

(i) other antiangiogenic agents including vascular targeting agents;
(ii) cytostatic agents;
(iii) biological response modifiers (for example interferon);
(iv) antibodies (for example edrecolomab); and
(v) antiproliferative/antineoplastic drugs and combinations thereof, as used in medical oncology; and other categories of agent are:
(vi) antisense therapies;
(vii) gene therapy approaches; and
(ix) immunotherapy approaches.

The invention is illustrated below by the following non-limiting examples:

EXAMPLE 1

| ZD6474 300 mg Coated Tablet Formulation (16 mm × 7.8 mm pillow shaped) | | |
|---|---|---|
| Ingredient | mg/tab | Function |
| Tablet core | | |
| ZD6474 | 300.0 | Active agent |
| Dibasic calcium phosphate[1] | 315 | Diluent |
| Microcrystalline cellulose[2] | 75 | Diluent |
| Crospovidone[3] | 37.5 | Disintegrant |

-continued

ZD6474 300 mg Coated Tablet Formulation
(16 mm × 7.8 mm pillow shaped)

| Ingredient | mg/tab | Function |
| --- | --- | --- |
| Povidone[4] | 15 | Binder |
| Magnesium stearate[5] | 7.5 | Lubricant |
| Total | 750.0 mg | |
| Tablet coating | | |
| Hydroxypropyl methylcellulose[6] | 14.7 mg | Film-forming agent |
| Polyethylene glycol 300[7] | 3.0 mg | Plasticiser |
| Titanium Dioxide[8] | 4.8 mg | Opacifier |

Footnotes: The following excipients were used in Example 1:

[1] Calipharm ® dibasic calcium phosphate (Rhodia Inc, Etoile Part-Dieu, France)

[2] Avicel ® microcrystalline cellulose (ex. FMC International, Philadelphia, Pennsylvania, USA).

[3] Polyplasdone ® crospovidone (International Speciality Products, Wayne, New Jersey, USA).

[4] Plasdone ® povidone K29-K32 (International Speciality Products, Wayne, New Jersey, USA).

[5] Magnesium Stearate ex. Mallinckrodt, St Louis, Missouri, USA.

[6] HPMC 606 Grade 2910, 6cP dynamic viscosity (measured at 2% w/v in water at 20° C.) ex Shin Etsu).

[7] Polyethylene glycol 300, Reagent Chemical Services Ltd (Runcorn UK).

[8] Titanium dioxide and a portion of the HPMC606 were provided in White Speedpaste 30001, Ansteads [address] or Opaspray White M-1-28813, Colorcon Ltd, Dartford, Kent, UK.

The formulation described as Example 1 was prepared by conventional wet granulation, compression and film coating processes. The ZD6474, dibasic calcium phosphate, microcrystalline cellulose, crospovidone and povidone were mixed together in a high shear granulator for 5 minutes to produce a homogeneous mix. 34% w/w of purified water was then added to the powders with 6 minutes total mixing time to produce a suitable wet mass. The wet granules were passed through a suitable screen to remove large particles and then dried. The dried granules were then passed through a further screen and blended with 1% w/w pre-milled magnesium stearate for 2.5 minutes. The resultant granules were compressed into tablet cores, which were then coated using a conventional pan coater. The film coat was applied by spraying an aqueous suspension of the hydroxypropyl methylcellulose, polyethylene glycol 300 and titanium dioxide onto the tablet cores.

Tablets of Example 1 formulation were compressed using a high-speed rotary press and tested using methods described previously. The following results were generated.

The mean hardness of the compressed tablets was 37.2 kp and the mean friability of 20 tablets was 0.13%. No tablet defects (including capping) were observed during the manufacture of these tablets.

Figure 2:
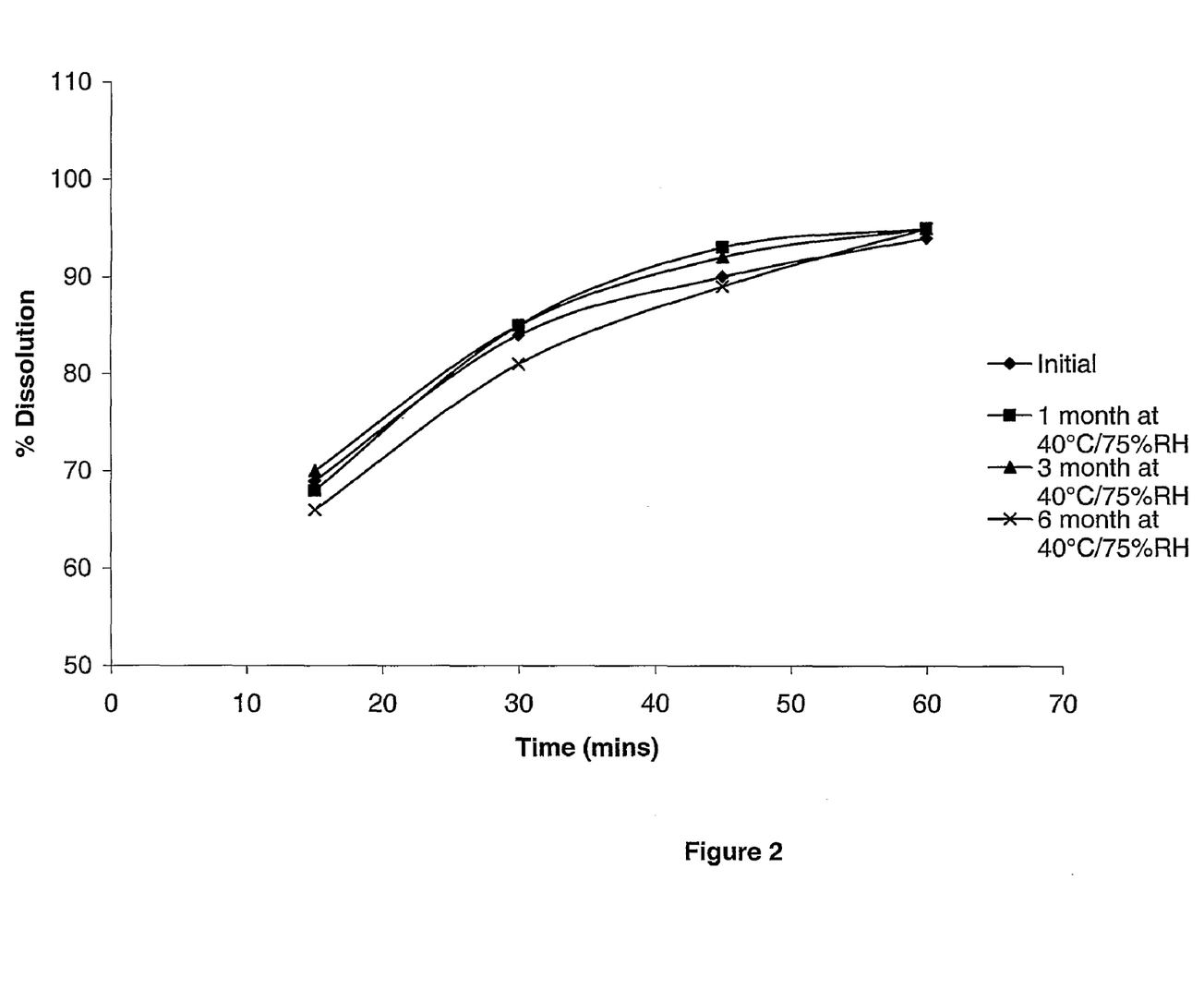
FIG. 2 shows dissolution profiles of the ZD6474 300 mg white film coated (WFC) tablets of Example 1 in 0.5% sodium lauryl sulphate at 37° C., before and after storage (in HDPE bottles) at elevated temperature and humidity.

The mean disintegration time of the tablets was 6 minutes. Dissolution profiles of the ZD6474 300 mg white film coated (WFC) tablets in 0.5% sodium lauryl sulphate at 37° C., before and after storage (in HDPE bottles) at elevated temperature and humidity are shown in FIG. 2.

No significant change was observed in the dissolution profiles of tablets after storage in HDPE bottles for up to 6 months at 40° C./75% Relative Humidity (RH).

EXAMPLE 2

Composition of ZD6474 400 mg tablet cores (Dibasic calcium phosphate/microcrystalline cellulose) (19 mm × 10 mm elliptical)

| Ingredient | mg/tab | Function |
| --- | --- | --- |
| ZD6474 | 400.0 | Active agent |
| Dibasic calcium phosphate | 417 | Diluent |
| Microcrystalline cellulose | 100 | Diluent |
| Sodium starch glycollate | 50 | Disintegrant |
| Povidone | 20 | Binder |
| Sodium lauryl sulphate | 3 | Wetting agent |
| Magnesium stearate | 10 | Lubricant |
| Total | 1000.0 mg | |

The formulation described as Example 2 was prepared by conventional wet granulation, compression and film coating processes, similar to that described above. The hardness of tablets compressed at 148 MPa was 29.9 kp. The disintegration time of these tables was 5.4 minutes. No tablet defects (including capping) were observed during the manufacture of these tablets.

EXAMPLE 3

Composition of ZD6474 400 mg tablet cores (Tribasic calcium phosphate/microcrystalline cellulose) (19 mm × 10 mm elliptical)

| Ingredient | mg/tab | Function |
| --- | --- | --- |
| ZD6474 | 400.0 | Active agent |
| Tribasic calcium phosphate | 417 | Diluent |
| Microcrystalline cellulose | 100 | Diluent |
| Sodium starch glycollate | 50 | Disintegrant |
| Povidone | 20 | Binder |
| Sodium lauryl sulphate | 3 | Wetting agent |
| Magnesium stearate | 10 | Lubricant |
| Total | 1000.0 mg | |

The formulation described as Example 3 was prepared by conventional wet granulation, compression and film coating processes. The tablets were compressed using a high-speed rotary press running at 100,000 tablets per hour and then tested using methods described previously.

The mean hardness of tablets compressed at a compaction pressure of 133 MPa was 27.3 kp. No tablet defects (including capping) were observed during the manufacture of these tablets. The mean disintegration time of tablets compressed at 133 MPa was 4.4 minutes.

EXAMPLE 4

| Composition of ZD6474 400 mg tablet cores (Dibasic calcium phosphate/pre-gelatinised starch) (19 mm × 10 mm elliptical) | | |
|---|---|---|
| Ingredient | mg/tab | Function |
| ZD6474 | 400.0 | Active agent |
| Dibasic calcium phosphate | 417 | Diluent |
| Pre-gelatinised starch | 100 | Diluent |
| Sodium starch glycollate | 50 | Disintegrant |
| Povidone | 20 | Binder |
| Sodium lauryl sulphate | 3 | Wetting agent |
| Magnesium stearate | 10 | Lubricant |
| Total | 1000.0 mg | |

The formulation described as Example 4 was prepared by conventional wet granulation, compression and film coating processes, similar to that described above. The hardness of tablets compressed at 142 MPa was 24.5 kp. The disintegration time of these tables was 4.9 minutes. No tablet defects (including capping) were observed during the manufacture of these tablets.

EXAMPLE 5

| Composition of ZD6474 200 mg tablet cores (Dibasic calcium phosphate/microcrystalline cellulose) (11 mm round) | | |
|---|---|---|
| Ingredient | mg/tab | Function |
| ZD6474 | 200.0 | Active agent |
| Dibasic calcium phosphate | 233.5 | Diluent |
| Microcrystalline cellulose | 25 | Diluent |
| Sodium starch glycollate | 25 | Disintegrant |
| Povidone | 10 | Binder |
| Sodium lauryl sulphate | 1.5. | Wetting agent |
| Magnesium stearate | 5 | Lubricant |
| Total | 500.0 mg | |

The formulation described as Example 5 was prepared by conventional wet granulation, compression and film coating processes, similar to that described above. The hardness of tablets compressed at 150 MPa was 17.4 kp. The disintegration time of these tables was 4.0 minutes. No tablet defects (including capping) were observed during the manufacture of these tablets at compression pressures of 150 MPa. Some capping was observed at high compression pressures (greater than 200 MPa).

The invention claimed is:

1. A pharmaceutical composition comprising:
    (a) 4-(4-bromo-2-fluoroanilino)-6-methoxy-7-(1-methylpiperidin-4-ylmethoxy)quinazoline (ZD6474) or a pharmaceutically acceptable salt thereof;
    (b) a brittle diluent selected from dibasic calcium phosphate, tribasic calcium phosphate, calcium phosphate anhydrous, calcium carbonate, calcium sulphate and magnesium oxide; and
    (c) a second diluent which is practically insoluble and has ductile compression properties selected from microcrystalline cellulose, starch, ethylcellulose and carboxymethylcellulose.

2. The pharmaceutical composition according to claim 1 wherein the brittle diluent is dibasic calcium phosphate.

3. The pharmaceutical composition according to claim 1 or claim 2 wherein the second diluent which is practically insoluble and has ductile compression properties is microcrystalline cellulose.

4. The pharmaceutical composition according to claim 1 comprising:
    (a) from 1 to 70 parts 4-(4-bromo-2-fluoroanilino)-6-methoxy-7-(1-methylpiperidin-4-ylmethoxy)quinazoline (ZD6474) or a pharmaceutically acceptable salt thereof;
    (b) from 1 to 96 parts of the brittle diluent; and
    (c) from 0.1 to 20 parts of the second diluent which is practically insoluble and has ductile compression properties;
    wherein all parts are by weight and the sum of the parts (a)+(b)+(c)=100.

5. The pharmaceutical composition according to claim 1 comprising:
    (a) from 5 to 50 parts 4-(4-bromo-2-fluoroanilino)-6-methoxy-7-(1-methylpiperidin-4-ylmethoxy)quinazoline (ZD6474) or a pharmaceutically acceptable salt thereof;
    (b) from 10 to 70 parts of the brittle diluent; and
    (c) from 1 to 15 parts of the second diluent which is practically insoluble and has ductile compression properties;
    wherein all parts are by weight and the sum of the parts (a)+(b)+(c)=100.

6. The pharmaceutical composition according to claim 4 or claim 5 wherein the brittle diluent is dibasic calcium phosphate and the second diluent which is practically insoluble and has ductile compression properties is microcrystalline cellulose.

* * * * *